United States Patent
Cai et al.

(10) Patent No.: US 10,208,060 B2
(45) Date of Patent: Feb. 19, 2019

(54) INHIBITORS OF HIF PROLYL HYDROXYLASE

(71) Applicants: Jiaqiang Cai, Shanghai (CN); Alejandro Crespo, Edison, NJ (US); John Debenham, Scotch Plains, NJ (US); Xiaoxing Du, Shanghai (CN); Ping Liu, Westfield, NJ (US); Rongqiang Liu, Shanghai (CN); Christina B. Madsen-Duggan, Scotch Plains, NJ (US); Weiguo Quan, Shanghai (CN); Christopher Sinz, Middletown, NJ (US); Liping Wang, Cranbury, NJ (US)

(72) Inventors: Jiaqiang Cai, Shanghai (CN); Alejandro Crespo, Edison, NJ (US); John Debenham, Scotch Plains, NJ (US); Xiaoxing Du, Shanghai (CN); Ping Liu, Westfield, NJ (US); Rongqiang Liu, Shanghai (CN); Christina B. Madsen-Duggan, Scotch Plains, NJ (US); Weiguo Quan, Shanghai (CN); Christopher Sinz, Middletown, NJ (US); Liping Wang, Cranbury, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 12 days.

(21) Appl. No.: 15/513,854

(22) PCT Filed: Sep. 23, 2015

(86) PCT No.: PCT/US2015/051570
§ 371 (c)(1),
(2) Date: Mar. 23, 2017

(87) PCT Pub. No.: WO2016/049098
PCT Pub. Date: Mar. 31, 2016

(65) Prior Publication Data
US 2017/0313718 A1 Nov. 2, 2017

(30) Foreign Application Priority Data
Sep. 28, 2014 (CN) .................. PCT/CN2014/087696

(51) Int. Cl.
*C07D 491/048* (2006.01)
*C07D 495/04* (2006.01)
*A61P 7/06* (2006.01)

(52) U.S. Cl.
CPC .............. *C07D 495/04* (2013.01); *A61P 7/06* (2018.01); *C07D 491/048* (2013.01)

(58) Field of Classification Search
CPC ................................................ C07D 491/048
See application file for complete search history.

(56) References Cited

U.S. PATENT DOCUMENTS

| 8,367,666 B2 | 2/2013 | Sasatani et al. |
| 8,372,863 B2 | 2/2013 | Clements et al. |
| 8,445,680 B2 | 5/2013 | Debenham et al. |
| 8,471,024 B2 | 6/2013 | Colandrea et al. |
| 2010/0331358 A1 | 12/2010 | Colandrea et al. |

FOREIGN PATENT DOCUMENTS

| WO | WO2009108496 | 9/2009 | |
| WO | WO2009108497 | 9/2009 | |
| WO | WO-2009108497 A1 * | 9/2009 | .......... C07D 495/04 |
| WO | WO2016049097 | 3/2016 | |
| WO | WO2016049098 | 3/2016 | |
| WO | WO2016049099 | 3/2016 | |
| WO | WO2016049100 | 3/2016 | |

OTHER PUBLICATIONS

Mayo Clinic. "Anemia." © 2017. Available from: < https://www.mayoclinic.org/diseases-conditions/anemia/symptoms-causes/syc-20351360?p=1 >.*
Silverman, R.B. "The Organic Chemistry of Drug Design and Drug Action." 2d ed. © 2004.*
Rabinowitz, Inhibition of Hypoxia-inducible Factor Prolyl Hydroxylase Domain Oxgen Sensors, Journal of Medicinal Chemistry, 2013, 9369-9402, vol. 56.

* cited by examiner

*Primary Examiner* — Andrew D Kosar
*Assistant Examiner* — John S Kenyon
(74) *Attorney, Agent, or Firm* — Matthew A. Leff; Laura M. Ginkel

(57) ABSTRACT

The present invention concerns compounds of formula I or a pharmaceutically acceptable salt thereof which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

(I)

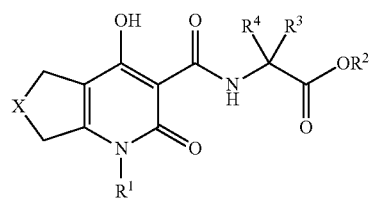

3 Claims, No Drawings
Specification includes a Sequence Listing.

INHIBITORS OF HIF PROLYL HYDROXYLASE

BACKGROUND OF THE INVENTION

The insufficient delivery of oxygen to cells and tissues is associated with anemia, which is defined as a deficiency in the blood's oxygen-carrying capacity, and ischemia, in which restrictions in blood supply are caused by a constriction or blockage of blood vessels. Anemia can be caused by the loss of red blood cells (hemorrhage), excessive red blood cell destruction (hemolysis) or deficiencies in erythropoiesis (production of red blood cells from precursors found in the bone marrow). The symptoms of anemia can include weakness, dizziness, fatigue, pallor, impairment of cognitive function and a general reduction in quality of life. Chronic and/or severe anemia can lead to the exacerbation of myocardial, cerebral or peripheral ischemia and to heart failure. Ischemia is defined as an absolute or relative shortage of oxygen to a tissue or organ and can result from disorders such as atherosclerosis, diabetes, thromboembolisms, hypotension, etc. The heart, brain and kidney are especially sensitive to ischemic stress caused by low blood supply.

The primary pharmacological treatment for anemia is administration of some variant of recombinant human erythropoietin (EPO). For anemias associated with kidney disease, chemotherapy-induced anemia, anemia from HIV-therapy or anemia due to blood loss, recombinant EPO is administered to enhance the supply of the hormone, correct the shortage of red blood cells and increase the blood's oxygen-carrying capacity. EPO replacement is not always sufficient to stimulate optimal erythropoiesis (e.g., in patients with iron processing deficiencies) and has associated risks.

Hypoxia-inducible factor (HIF) has been identified as a primary regulator of the cellular response to low oxygen. HIF is a heterodimeric gene transcription factor consisting of a highly regulated α-subunit (HIF-α) and a constitutively expressed β-subunit (HIF-β, also known as ARNT, or aryl hydrocarbon receptor nuclear transporter). HIF target genes are reported to be associated with various aspects of erythropoiesis (e.g., erythropoietin (EPO) and EPO receptor), glycolysis and angiogenesis (e.g., vascular endothelial growth factor (VEGF)). Genes for proteins involved in iron absorption, transport and utilization as well as heme synthesis are also targets of HIF.

Under normal oxygenation, HIF-α is a substrate in a reaction with molecular oxygen, which is catalyzed by a family of iron(II)-, 2-ketoglutarate- and ascorbate-dependent dioxygenase enzymes called PHD-1 (EGLN2), or egg laying abnormal 9 homolog 2, PHD2 (EGLN1), and PHD3 (EGLN3). Proline residues of HIF-α are hydroxylated (e.g., Pro-402 and Pro-564 of HIF-1α) and the resulting product is a target of the tumor suppressor protein von-Hippel Lindau, a component of an E3 ubiquitin ligase multiprotein complex involved in protein ubiquitination. Under low oxygenation, the HIF-α hydroxylation reaction is less efficient and HIF-α is available to dimerize with HIF-β. HIF dimers are translocated to the cell nucleus where they bind to a hypoxia-responsive enhancer element of HIF target genes.

Cellular levels of HIF are known to increase under conditions of hypoxia and after exposure to hypoxia mimetic agents. The latter includes, but is not limited to, specific metal ions (e.g., cobalt, nickel, manganese), iron chelators (e.g., desferrioxamine) and analogs of 2-ketoglurate (e.g., N-oxalyl glycine). The compounds of the present invention inhibit the HIF prolyl hydroxylases (PHD-1, PHD-2, PHD-3) and can also serve to modulate HIF levels. These compounds therefore have utility for the treatment and/or prevention of disorders or conditions where HIF modulation is desirable, such as anemia and ischemia. As an alternative to recombinant erythropoietin therapy, the compounds of the present invention provide a simpler and broader method for the management of anemia.

SUMMARY OF THE INVENTION

The present invention concerns compounds of formula I

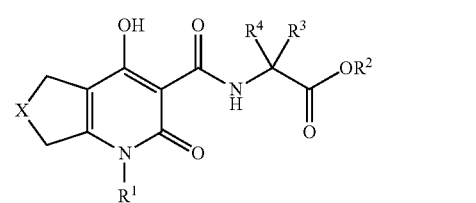

or a pharmaceutically acceptable salt thereof, which inhibit HIF prolyl hydroxylase, their use for enhancing endogenous production of erythropoietin, and for treating conditions associated with reduced endogenous production of erythropoietin such as anemia and like conditions, as well as pharmaceutical compositions comprising such a compound and a pharmaceutical carrier.

DETAILED DESCRIPTION OF THE INVENTION

The present invention provides compounds of formula I or a pharmaceutically acceptable salt thereof:

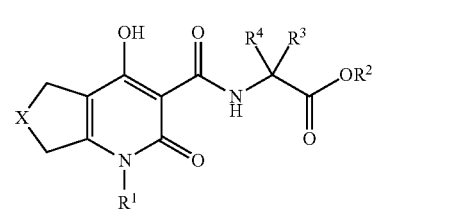

wherein:

X is O or S;

$R^1$ is selected from aryl and heterocyclyl, said aryl and heterocyclyl are optionally substituted with 1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;

$R^2$ is hydrogen or methyl;

$R^3$ and $R^4$ are each independently chosen from hydrogen, hydroxyl, and $C_{1-4}$alkyl; and $R^b$ is independently hydrogen or $C_{1-4}$ alkyl.

In another embodiment the present invention provides compounds of formula II or a pharmaceutically acceptable salt thereof:

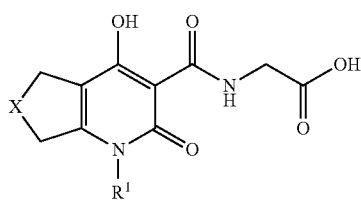

wherein:
X is O or S;
R¹ is selected from aryl and heterocyclyl, said aryl and heterocyclyl are optionally substituted with 1, 2, or 3 substituents chosen from: halogen, CHF$_2$, OCHF$_2$, CF$_3$, OCF$_3$, CN, C$_{1-4}$ alkyl, O(C$_{1-4}$)alkyl, S(O)$_2$R$^b$, C(O)N(R$^b$)$_2$, phenyl, wherein said alkyl and phenyl are optionally substituted with 1, 2, or 3 substituents chosen from: OH, CF$_3$, OCF$_3$, halogen, C(O)N(R$^b$)$_2$, and CN; and
R$^b$ is independently hydrogen or C$_{1-4}$ alkyl.

Illustrative but nonlimiting examples of compounds of the invention are the following:
2-(4-Hydroxy-2-oxo-1-(4-(trifluoromethyl)phenyl)-1,2,5,7-tetrahydrofuro[3,4-b]pyridine-3-carboxamido)acetic acid;
2-(1-(4-chlorophenyl)-4-hydroxy-2-oxo-1,2,5,7-tetrahydrofuro[3,4-b]pyridine-3-carboxamido)acetic acid;
2-(1-(4-fluorophenyl)-4-hydroxy-2-oxo-1,2,5,7-tetrahydrofuro[3,4-b]pyridine-3-carboxamido)acetic acid;
2-(4-hydroxy-2-oxo-1-phenyl-1,2,5,7-tetrahydrofuro[3,4-b]pyridine-3-carboxamido)acetic acid;
2-(4-hydroxy-1-(4-methoxyphenyl)-2-oxo-1,2,5,7-tetrahydrofuro[3,4-b]pyridine-3-carboxamido)acetic acid;
2-(4-hydroxy-2-oxo-1-(4-(trifluoromethoxy)phenyl)-1,2,5,7-tetrahydrofuro[3,4-b]pyridine-3-carboxamido)acetic acid;
2-(4-hydroxy-2-oxo-1-(m-tolyl)-1,2,5,7-tetrahydrofuro[3,4-b]pyridine-3-carboxamido)acetic acid;
2-(4-hydroxy-2-oxo-1-(p-tolyl)-1,2,5,7-tetrahydrofuro[3,4-b]pyridine-3-carboxamido)acetic acid;
2-(1-(4-cyanophenyl)-4-hydroxy-2-oxo-1,2,5,7-tetrahydrofuro[3,4-b]pyridine-3-carboxamido)acetic acid;
2-(4-hydroxy-1-(5-methoxypyridin-2-yl)-2-oxo-1,2,5,7-tetrahydrofuro[3,4-b]pyridine-3-carboxamido)acetic acid;
2-(1-(4-Bromophenyl)-4-hydroxy-2-oxo-1,2,5,7-tetrahydrothieno[3,4-b]pyridine-3-carboxamido)acetic acid;
2-(4-Hydroxy-2-oxo-1-((4'-(trifluoromethoxy)-[1,1'-biphenyl]-4-yl)methyl)-1,2,5,7-tetrahydrothieno[3,4-b]pyridine-3-carboxamido)acetic acid; and
2-(4-Hydroxy-2-oxo-1-(3'-(trifluoromethoxy)-[1,1'-biphenyl]-4-yl)-1,2,5,7-tetrahydrothieno[3,4-b]pyridine-3-carboxamido)acetic acid;
or a pharmaceutically acceptable salt thereof.

As used herein except where noted, "alkyl" is intended to include both branched- and straight-chain saturated aliphatic hydrocarbon groups, including all isomers, having the specified number of carbon atoms. Commonly used abbreviations for alkyl groups are used throughout the specification, e.g. methyl may be represented by "Me" or CH$_3$, ethyl may be represented by "Et" or CH$_2$CH$_3$, propyl may be represented by "Pr" or CH$_2$CH$_2$CH$_3$, butyl may be represented by "Bu" or CH$_2$CH$_2$CH$_2$CH$_3$, etc. "C$_{1-4}$ alkyl" (or "C$_1$-C$_4$ alkyl") for example, means linear or branched chain alkyl groups, including all isomers, having the specified number of carbon atoms. "C$_{1-4}$ alkyl" includes n-, iso-, sec- and t-butyl, n- and isopropyl, ethyl and methyl.

The term "halogen" (or "halo") refers to fluorine, chlorine, bromine and iodine (alternatively referred to as fluoro (F), chloro (Cl), bromo (Br), and iodo (I)).

The term "aryl" refers to aromatic mono- and polycarbocyclic ring systems, wherein the individual carbocyclic rings in the polyring systems are fused or attached to each other via a single bond. Suitable aryl groups include phenyl, naphthyl, and biphenylenyl.

The term "carbocycle" (and variations thereof such as "carbocyclic" or "carbocyclyl") as used herein, unless otherwise indicated, refers to (i) a C$_3$ to C$_8$ monocyclic, saturated or unsaturated ring or (ii) a C$_7$ to C$_{12}$ bicyclic saturated or unsaturated ring system. Each ring in (ii) is either independent of, or fused to, the other ring, and each ring is saturated or unsaturated. The carbocycle may be attached to the rest of the molecule at any carbon atom which results in a stable compound. The fused bicyclic carbocycles are a subset of the carbocycles; i.e., the term "fused bicyclic carbocycle" generally refers to a C$_7$ to C$_{10}$ bicyclic ring system in which each ring is saturated or unsaturated and two adjacent carbon atoms are shared by each of the rings in the ring system. A fused bicyclic carbocycle in which one ring is saturated and the other is saturated is a saturated bicyclic ring system. A fused bicyclic carbocycle in which one ring is benzene and the other is saturated is an unsaturated bicyclic ring system. A fused bicyclic carbocycle in which one ring is benzene and the other is unsaturated is an unsaturated ring system. Saturated carbocyclic rings are also referred to as cycloalkyl rings, e.g., cyclopropyl, cyclobutyl, etc. A subset of the fused bicyclic unsaturated carbocycles are those bicyclic carbocycles in which one ring is a benzene ring and the other ring is saturated or unsaturated, with attachment via any carbon atom that results in a stable compound. Representative examples of this subset include the following:

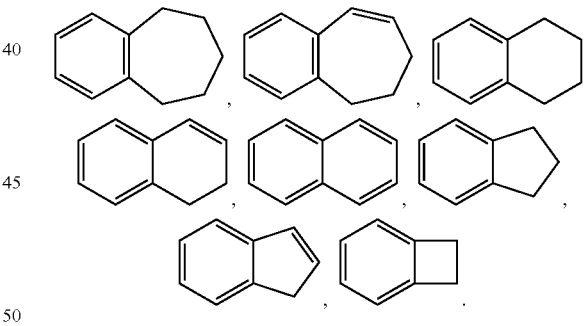

The term "heterocycle" (and variations thereof such as "heterocyclic" or "heterocyclyl") broadly refers to (i) a stable 4- to 8-membered, saturated or unsaturated monocyclic ring, or (ii) a stable 7- to 12-membered bicyclic ring system, wherein each ring in (ii) is independent of, or fused to, the other ring or rings and each ring is saturated or unsaturated, and the monocyclic ring or bicyclic ring system contains one or more heteroatoms (e.g., from 1 to 6 heteroatoms, or from 1 to 4 heteroatoms) selected from N, O and S and a balance of carbon atoms (the monocyclic ring typically contains at least one carbon atom and the ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Unless otherwise specified, when the heterocyclic ring has substituents, it is understood that the substituents may be attached to any atom in the ring, whether a heteroatom or a carbon atom, provided that a stable chemical structure results.

Non limiting examples of heterocyclylic moieties include, but are not limited to, the following: azepanyl, azabenzimidazole, benzoimidazolyl, benzofuryl, benzofurazanyl, benzopyrazolyl, benzothiazolyl, benzothienyl, benzotriazolyl, benzothiophenyl, benzoxazolyl, carbazolyl, carbolinyl, chromanyl, cinnolinyl, furanyl, imidazolyl, indolinyl, indolyl, indolazinyl, indazolyl, isobenzofuryl, isochromanyl, isoindolyl, isoquinolyl, isothiazolyl, isoxazolyl, naphthpyridinyl, oxadiazolyl, oxazolyl, oxazolinyl, isooxazolinyl, oxetanyl, pyranyl, pyrazinyl, pyrazolidinyl, pyrazolyl, pyridazinyl, pyridopyridinyl, pyridazinyl, pyridinyl, pyrimidyl, pyrrolyl, quinazolinyl, quinolyl, quinoxalinyl, quinoxalinyl, tetrahydropyranyl, tetrahydroisoquinolinyl, tetrazolyl, tetrazolopyridyl, thiadiazolyl, thiazolyl, thienyl, triazolyl, azetidinyl, aziridinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuryl, dihydrobenzothiophenyl, dihydrobenzoxazolyl, dihydrofuryl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, tetrahydroquinolinyl, tetrahydroisoquinolinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuryl, tetrahydrothienyl, tetrahydroquinolinyl, 2,3-dihydrobenzofuryl, 2,3-dihydrobenzo-1,4-dioxinyl, imidazo(2,1-b)(1,3)thiazole, and benzo-1,3-dioxolyl.

Saturated heterocyclics form a subset of the heterocycles; i.e., the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring or a stable 7- to 12-membered bicyclic ring system which consists of carbon atoms and one or more heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Heteroaromatics form another subset of the heterocycles; i.e., the term "heteroaromatic" (alternatively "heteroaryl") generally refers to a heterocycle as defined above in which the entire ring system (whether mono- or poly-cyclic) is an aromatic ring system. The term "heteroaromatic ring" refers a 5- or 6-membered monocyclic aromatic ring or a 7- to 12-membered bicyclic which consists of carbon atoms and one or more heteroatoms selected from N, O and S. In the case of substituted heteroaryl rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuryl, 2,3-dihydrobenzo-1,4-dioxinyl

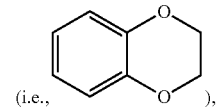

(i.e., ), imidazo(2,1-b)(1,3)thiazole

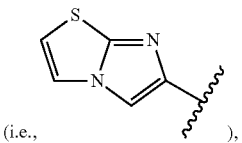 [SMILES: *c1cn2ccsc2n1]

(i.e., ), and benzo-1,3-dioxolyl

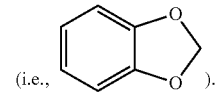

(i.e., ).

In certain contexts herein,

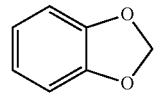

is alternatively referred to as phenyl having as a substituent methylenedioxy attached to two adjacent carbon atoms.

Unless expressly stated to the contrary, all ranges cited herein are inclusive. For example, a heterocycle described as containing from "1 to 4 heteroatoms" means the heterocycle can contain 1, 2, 3 or 4 heteroatoms.

When any variable occurs more than one time in any constituent or in any formula depicting and describing compounds of the invention, its definition on each occurrence is independent of its definition at every other occurrence. Also, combinations of substituents and/or variables are permissible only if such combinations result in stable compounds.

The term "substituted" (e.g., as in "aryl which is optionally substituted with one or more substituents . . . ") includes mono- and poly-substitution by a named substituent to the extent such single and multiple substitution (including multiple substitution at the same site) is chemically allowed.

When any variable (e.g., $R^b$, etc.) occurs more than one time in any substituent or in formulas I-II, its definition in each occurrence is independent of its definition at every other occurrence. Also, combinations of substituents and/or variables are permissible only if such combinations result in stable compounds.

In choosing compounds of the present invention, one of ordinary skill in the art will recognize that the various substituents, i.e. $R^1$, $R^2$, $R^3$, etc., are to be chosen in conformity with well-known principles of chemical structure connectivity.

Lines drawn into the ring systems from substituents indicate that the indicated bond can be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups can be on the same carbon or on different carbons, so long as a stable structure results. The phrase "optionally substituted with one or more substituents" should be taken to be equivalent to the phrase "optionally substituted with at least one substituent" and in such cases one embodiment will have from zero to three substituents.

In another embodiment of the invention is a compound of formulas I and II or a pharmaceutically acceptable salt thereof wherein:
X is O or S;
$R^1$ is selected from aryl and heterocyclyl, said aryl and heterocyclyl are optionally substituted with
1, 2, or 3 substituents chosen from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN;
$R^2$ is hydrogen or methyl;
$R^3$ and $R^4$ are each independently chosen from hydrogen, hydroxyl, and $C_{1-4}$alkyl;
$R^b$ is independently hydrogen or $C_{1-4}$ alkyl.
In another embodiment of the invention, X is O.
In another embodiment of the invention, X is S.
In another embodiment of the invention, $R^1$ is selected from:

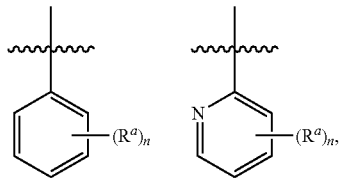

wherein $R^a$ is independently selected from: halogen, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, halogen, $C(O)N(R^b)_2$, and CN.
n is 0, 1, 2 or 3.
$R^b$ is independently hydrogen or $C_{1-4}$ alkyl.
Or, wherein $R^a$ is independently selected from: Cl, F, Br, $CHF_2$, $OCHF_2$, $CF_3$, $OCF_3$, CN, $C_{1-4}$ alkyl, $O(C_{1-4})$alkyl, $S(O)_2R^b$, $C(O)N(R^b)_2$, phenyl, wherein said alkyl and phenyl are optionally substituted with 1, 2, or 3 substituents chosen from: OH, $CF_3$, $OCF_3$, Cl, F, $C(O)N(R^b)_2$, and CN.
n is 0, 1, 2 or 3.
$R^b$ is independently hydrogen or $C_{1-4}$ alkyl.
Or, wherein $R^a$ is independently selected from: Cl, F, Br, $CF_3$, $OCF_3$, CN, $C_{1-4}$ alkyl, $O(C_{1-4})$alkyl, phenyl, wherein said alkyl and phenyl are optionally substituted with 1, 2, or 3 substituents chosen from: OH, $CF_3$, $OCF_3$, Cl, F, $C(O)N(R^b)_2$, and CN.
n is 0, 1, 2 or 3.

$R^b$ is independently hydrogen or $C_{1-4}$ alkyl.
Or, wherein $R^a$ is independently selected from: Cl, F, Br, $CF_3$, $OCF_3$, CN, Me, O-Me, phenyl, wherein said phenyl is optionally substituted $OCF_3$.
n is 0 or 1.
In another embodiment of the invention, n is 0, 1, 2 or 3.
In another embodiment of the invention, n is 0, 1 or 2.
In another embodiment of the invention, n is 0 or 1.
In another embodiment of the invention, $R^2$ is hydrogen.
In another embodiment of the invention, $R^3$ is hydrogen.
In another embodiment of the invention, $R^4$ is hydrogen.

Optical Isomers-Diastereomers-Geometric Isomers-Tautomers

Compounds described herein may contain an asymmetric center and may thus exist as enantiomers. Where the compounds according to the invention possess two or more asymmetric centers, they may additionally exist as diastereomers. The present invention includes all such possible stereoisomers as substantially pure resolved enantiomers, racemic mixtures thereof, as well as mixtures of diastereomers. The above Formula I is shown without a definitive stereochemistry at certain positions. The present invention includes all stereoisomers of Formula I and pharmaceutically acceptable salts and solvates thereof. Unless specifically mentioned otherwise, reference to one isomer applies to any of the possible isomers. Whenever the isomeric composition is unspecified, all possible isomers are included. Diastereoisomeric pairs of enantiomers may be separated by, for example, fractional crystallization from a suitable solvent, and the pair of enantiomers thus obtained may be separated into individual stereoisomers by conventional means, for example by the use of an optically active acid or base as a resolving agent or on a chiral HPLC column. Further, any enantiomer or diastereomer of a compound of the general Formula I may be obtained by stereospecific synthesis using optically pure starting materials or reagents of known configuration.

When compounds described herein contain olefinic double bonds, unless specified otherwise, such double bonds are meant to include both E and Z geometric isomers.

Some of the compounds described herein may exist with different points of attachment of hydrogen, referred to as tautomers. For example, compounds including carbonyl —$CH_2C(O)$— groups (keto forms) may undergo tautomerism to form hydroxy-CH=C(OH)— groups (enol forms). Both keto and enol forms, individually as well as mixtures thereof, are included within the scope of the present invention.

Salts

Pharmaceutically acceptable salts include both the metallic (inorganic) salts and organic salts; a list of which is given in Remington's Pharmaceutical Sciences, 17th Edition, pg. 1418 (1985). It is well known to one skilled in the art that an appropriate salt form is chosen based on physical and chemical stability, flowability, hydro-scopicity and solubility. The term "pharmaceutically acceptable salts" refers to salts prepared from pharmaceutically acceptable non-toxic bases or acids. When the compound of the present invention is acidic, its corresponding salt can be conveniently prepared from inorganic bases or organic bases. Salts derived from such inorganic bases include aluminum, ammonium, calcium, copper (ic and ous), ferric, ferrous, lithium, magnesium, manganese (ic and ous), potassium, sodium, zinc and the like salts. Preferred are the ammonium, calcium, magnesium, potassium and sodium salts. Salts prepared from organic bases include salts of primary, secondary, and tertiary amines derived from both naturally occurring and synthetic sources. Pharmaceutically acceptable organic non-toxic bases from which salts can be formed include, for example, arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, dicyclohexylamine, lysine, methyl-glucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from inorganic or organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methane-sulfonic, mucic, nitric, pamoic, pantothenic, phosphoric, succinic, sulfuric, tartaric, p-toluene-sulfonic acid and the like. Preferred are citric, hydrobromic, hydrochloric, maleic, phosphoric, sulfuric, and tartaric acids.

Solvates

The present invention includes within its scope solvates of compounds of Formula I. As used herein, the term "solvate" refers to a complex of variable stoichiometry formed by a solute (i.e., a compound of Formula I) or a pharmaceutically acceptable salt thereof and a solvent that does not interfere with the biological activity of the solute. Examples of solvents include, but are not limited to water, ethanol, and acetic acid. When the solvent is water, the solvate is known as hydrate; hydrate includes, but is not limited to, hemi-, mono, sesqui-, di- and trihydrates.

Prodrugs

The present invention includes within its scope the use of prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with a compound of formula I or with a compound which may not be a compound of formula I, but which converts to a compound of formula I in vivo after administration to the patient. Conventional procedures for the selection and preparation of suitable prodrug derivatives are described, for example, in "Design of Prodrugs," ed. H. Bundgaard, Elsevier, 1985.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Utilities

Compounds of the present invention are inhibitors of hypoxia-inducible factor (HIF) prolyl hydroxylases, and as such are useful in the treatment and prevention of diseases and conditions in which HIF modulation is desirable, such as anemia and ischemia. Compounds of the invention can be used in a selective and controlled manner to induce hypoxia-inducible factor stabilization and to rapidly and reversibly stimulate erythropoietin production and secretion. Accordingly, another aspect of the present invention provides a method of treating or preventing a disease or condition in a mammal, the treatment or prevention of which is effected or facilitated by HIF prolyl hydroxylase inhibition, which comprises administering an amount of a compound of Formula I that is effective for inhibiting HIF prolyl hydroxylase. This aspect of the present invention further includes the use of a compound of Formula I in the manufacture of a medicament for the treatment or prevention of a disease or condition modulated by HIF prolyl hydroxylase.

In one embodiment is a method of enhancing endogenous production of erythropoietin in a mammal which comprises administering to said mammal an amount of a compound of Formula I that is effective for enhancing endogenous production of erythropoietin.

Another embodiment is a method of treating anemia in a mammal which comprises administering to said mammal a therapeutically effective amount of a compound of Formula I. "Anemia" includes, but is not limited to, chronic kidney disease anemia, chemotherapy-induced anemia (e.g., anemia resulting from antiviral drug regimens for infectious diseases, such as HIV and hepatitis C virus), anemia of chronic disease, anemia associated with cancer conditions, anemia resulting from radiation treatment for cancer, anemias of chronic immune disorders such as rheumatoid arthritis, inflammatory bowel disease, and lupus, and anemias due to menstruation or of senescence or in other individuals with iron processing deficiencies such as those who are iron-replete but unable to utilize iron properly.

Another embodiment is a method of treating ischemic diseases in a mammal, which comprises administering to said mammal a therapeutically effective amount of a compound of Formula I.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Route of Administration/Dosage

The compounds of this invention can be administered for the treatment or prevention of afflictions, diseases and illnesses according to the invention by any means that effects contact of the active ingredient compound with the site of action in the body of a warm-blooded animal. For example, administration can be oral, topical, including transdermal, ocular, buccal, intranasal, inhalation, intravaginal, rectal, intracisternal and parenteral. The term "parenteral" as used herein refers to modes of administration which include subcutaneous, intravenous, intramuscular, intraarticular injection or infusion, intrasternal and intraperitoneal. For the purpose of this disclosure, a warm-blooded animal is a member of the animal kingdom possessed of a homeostatic mechanism and includes mammals and birds.

The compounds can be administered by any conventional means available for use in conjunction with pharmaceuticals, either as individual therapeutic agents or in a combination of therapeutic agents. They can be administered alone, but are generally administered with a pharmaceutical carrier selected on the basis of the chosen route of administration and standard pharmaceutical practice.

The dosage administered will be dependent on the age, health and weight of the recipient, the extent of disease, kind of concurrent treatment, if any, frequency of treatment and the nature of the effect desired. Usually, a daily dosage of active ingredient compound will be from about 0.1-2000 milligrams per day. Ordinarily, from 10 to 500 milligrams per day in one or more applications is effective to obtain desired results. These dosages are the effective amounts for the treatment and prevention of afflictions, diseases and illnesses described above, e.g., anemia.

Pharmaceutical Composition

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

The pharmaceutical compositions of the present invention comprise a compound represented by Formula I (or a pharmaceutically acceptable salt or solvate thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

The active ingredient can be administered orally in solid dosage forms, such as capsules, tablets, troches, dragées, granules and powders, or in liquid dosage forms, such as elixirs, syrups, emulsions, dispersions, and suspensions. The active ingredient can also be administered parenterally, in sterile liquid dosage forms, such as dispersions, suspensions or solutions. Other dosages forms that can also be used to administer the active ingredient as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propylparaben, and chlorobutanol.

Suitable pharmaceutical carriers are described in *Remington's Pharmaceutical Sciences*, A. Osol, a standard reference text in this field.

For administration by inhalation, the compounds of the present invention may be conveniently delivered in the form of an aerosol spray presentation from pressurized packs or nebulisers. The compounds may also be delivered as powders which may be formulated and the powder composition may be inhaled with the aid of an insufflation powder inhaler device. The preferred delivery system for inhalation is a metered dose inhalation (MDI) aerosol, which may be formulated as a suspension or solution of a compound of Formula I in suitable propellants, such as fluorocarbons or hydrocarbons.

For ocular administration, an ophthalmic preparation may be formulated with an appropriate weight percent solution or suspension of the compounds of Formula I in an appropriate ophthalmic vehicle, such that the compound is maintained in contact with the ocular surface for a sufficient time period to allow the compound to penetrate the corneal and internal regions of the eye.

Useful pharmaceutical dosage-forms for administration of the compounds of this invention include, but are not limited to, hard and soft gelatin capsules, tablets, parenteral injectables, and oral suspensions.

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

A parenteral composition suitable for administration by injection is prepared by stirring 1.5% by weight of active ingredient in 10% by volume propylene glycol. The solution is made to volume with water for injection and sterilized.

An aqueous suspension is prepared for oral administration so that each 5 milliliters contain 100 milligrams of finely divided active ingredient, 100 milligrams of sodium carboxymethyl cellulose, 5 milligrams of sodium benzoate, 1.0 grams of sorbitol solution, U.S.P., and 0.025 milliliters of vanillin.

The same dosage forms can generally be used when the compounds of this invention are administered stepwise or in conjunction with another therapeutic agent. When drugs are administered in physical combination, the dosage form and administration route should be selected depending on the compatibility of the combined drugs. Thus the term coadministration is understood to include the administration of the two agents concomitantly or sequentially, or alternatively as a fixed dose combination of the two active components.

Compounds of the invention can be administered as the sole active ingredient or in combination with a second active ingredient, including other active ingredients known to be useful for improving the level of erythropoietin in a patient.

Abbreviations Used in the Description of the Preparation of the Compounds of the Present Invention:
~ Approximately
AcOH Acetic acid
$Ag_2O$ Silver oxide
AIBN 2,2'-azobis(2-methylpropionitrile)
Aq Aqueous
Bn Benzyl
BnBr Benzylbromide
BnCl Benzylchloride
BnOH Benzylalcohol
$Boc_2O$ or di-tert-butyl dicarbonate
$BOC_2O$
Brine Saturated aqueous sodium chloride solution
BuLi n-butyl lithium
CDI Carbonyl diimidazole
DBU 1,8-diazabicyclo[5.4.0]undec-7-ene
DCC N,N'-dicyclohexylcarbodiimide
DEAD diethylazodicarboxylate
DCM Dichloromethane
DIPEA N,N-diisopropylethylaime
DMAP 4-N,N-dimethylaminopyridine
DMF N,N-dimethylformamide
DMSO Dimethyl sulfoxide
DPPA Diphenyl phosphoryl azide
EDC or EDCI 1-(3-dimethylaminopropyl)-3-ethylcarbodiimide hydrogenchloride salt
EtOAc or EA Ethyl acetate
Et (et) Ethyl
EtOH Ethanol
$Et_2O$ or ether Diethyl ether
$Et_3N$ triethylamine
G Gram
h or hr Hour
HATU O-(7-Azabenzotriazol-1-yl)-N,N,N',N'-tetramethyluronium hexafluorophosphate
HCl Hydrochloric acid
HOBt 1-hydroxybenzotriazole
HPLC High-performance liquid chromatography
i-propanol Isopropyl alcohol
i-PrOH or IPA Isopropyl alcohol
$K_2CO_3$ Potassium carbonate
KOH Potassium hydroxide
LCMS Liquid chromatography mass spectrometry
LiOH Lithium hydroxide
Mg Milligrams
mL Milliliters
Mmol Millimole
MeCN Acetonitrile
MeOH Methanol
Min Minutes
ms or MS Mass spectrum
Mg Microgram(s)
µL Microliters
NaOEt Sodium ethoxide
NaOMe Sodium methoxide
$Na_2SO_4$ Sodium sulfate
NBS N-bromosuccinimide
NHAc Acetamido
NHCbz Benzyloxycarboxamido
NaOH Sodium hydroxide
$NaN_3$ Sodium azide
$NH_4OH$ ammonium hydroxide
NMP N-methylpyrrolidone
Pd/C Palladium on carbon
$Pd(OH)_2$ Palladium hydroxide
$Pd(PPh_3)_4$ Palladium tetrakis(triphenylphosphine)
PE Petroleum ether
PhLi Phenyl lithium
PG Protecting group
Ph Phenyl group
PMB Para-methoxybenzyl
PPTS Pyridinium Para-toluenesulfonate
$PPh_3$ Triphenyphosphine
$R_t$ Retention time
RT or rt Room temperature
$SOCl_2$ Thionyl chloride
TEA Triethylamine
TFA Trifluoroacetic acid
THF Tetrahydrofuran
TBTU O-(Benzotriazol-1-yl)-N,N,N',N'-tetramethyluronium tetrafluoroborate
TMS Trimethylsilyl
TMSBr Trimethylsilyl bromide
TMSCN Trimethylsilyl cyanide
$TMSCHN_2$ (trimethylsilyl)diazomethane
TsCl Para-toluenesulfonyl chloride The compounds of this invention may be prepared by employing reactions as shown in the following schemes, in addition to other standard manipulations that are known in the literature or exemplified in the experimental procedures. The illustrative schemes below, therefore, are not limited by the compounds listed or by any particular substituents employed for illustrative purposes. Substituent numbering as shown in the schemes does not necessarily correlate to that used in the claims and often, for clarity, a single substituent is shown attached to the compound in place of multiple substituents which are allowed under the definitions of Formula I defined previously.

General Experimental Comments

Reactions sensitive to moisture or air were performed under nitrogen using anhydrous solvents and reagents. The progress of reactions was determined by either analytical thin layer chromatography (TLC) performed with E. Merck precoated TLC plates, silica gel 60F-254, layer thickness 0.25 mm or liquid chromatography-mass spectrum (LC-MS). Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 μm 3.0×50 mm column with gradient 10:90-100 v/v CH$_3$CN/H$_2$O+v 0.05% TFA over 3.75 min then hold at 100 CH$_3$CN+v 0.05% TFA for 1.75 min; flow rate 1.0 mL/min, UV wavelength 254 nm). Concentration of solutions was carried out on a rotary evaporator under reduced pressure. Flash chromatography was performed using a Biotage Flash Chromatography apparatus (Dyax Corp.) on silica gel (32-63 mM, 60 Å pore size) in pre-packed cartridges. $^1$H-NMR spectra were obtained on a 400 or 500 MHz VARIAN Spectrometer in CDCl$_3$ or CD$_3$OD or other solvents as indicated and chemical shifts are reported as δ using the solvent peak as reference and coupling constants are reported in hertz (Hz).

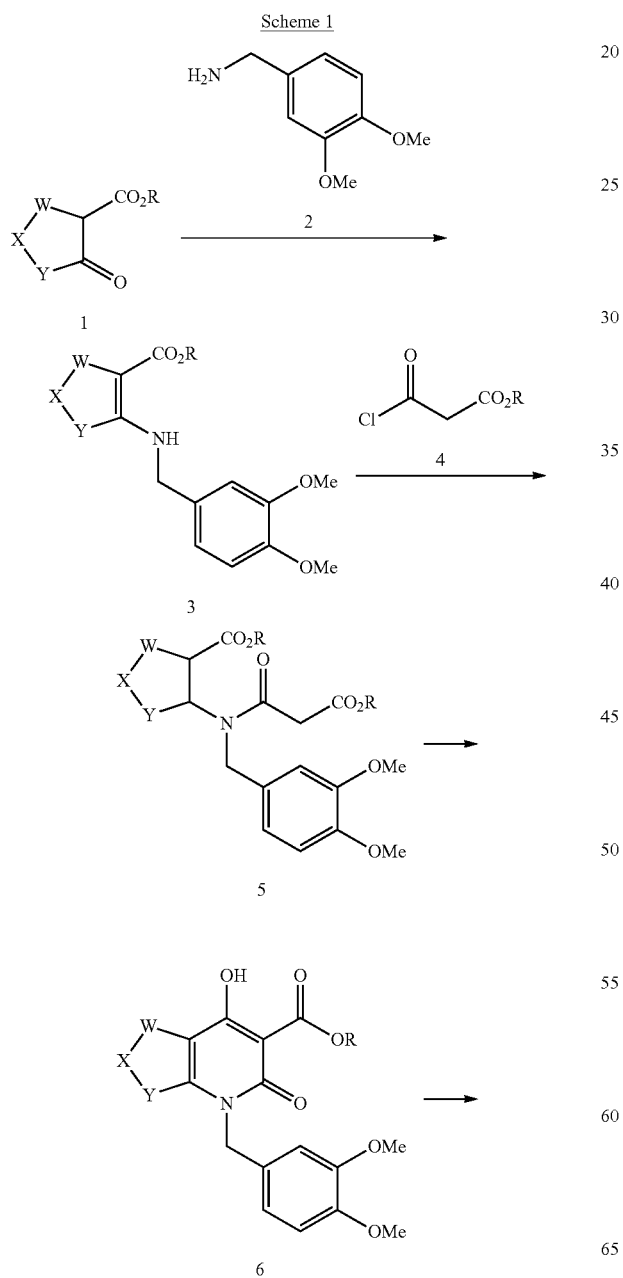

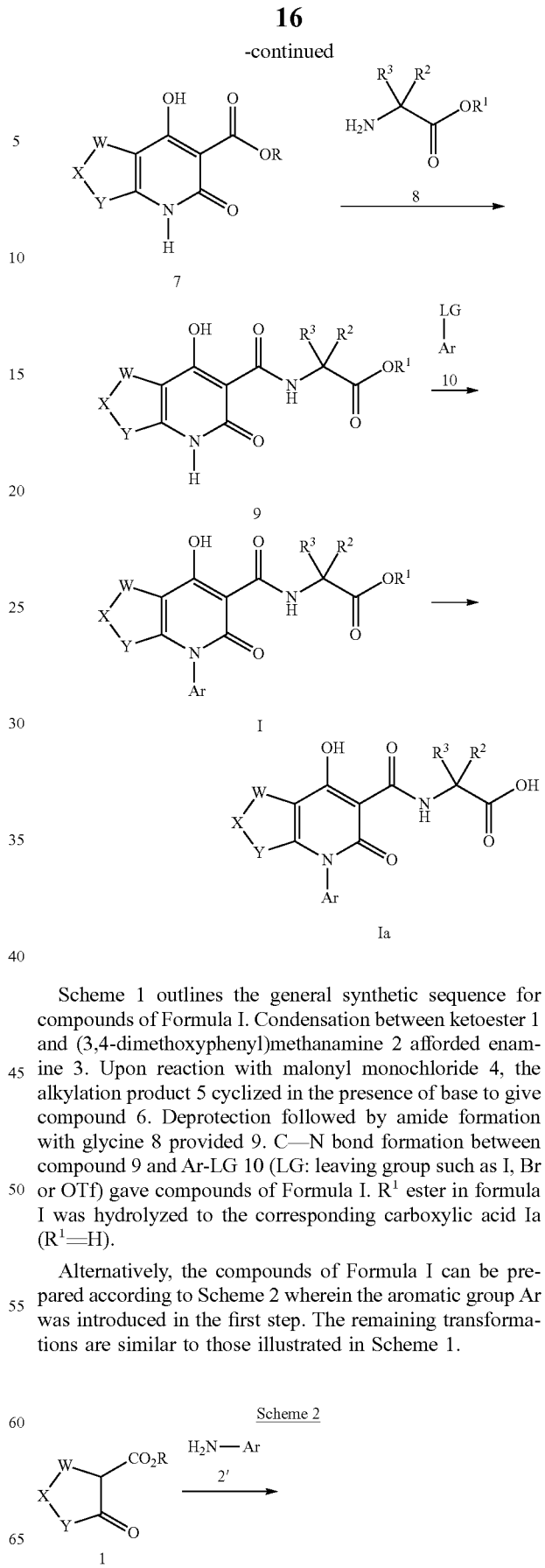

Scheme 1 outlines the general synthetic sequence for compounds of Formula I. Condensation between ketoester 1 and (3,4-dimethoxyphenyl)methanamine 2 afforded enamine 3. Upon reaction with malonyl monochloride 4, the alkylation product 5 cyclized in the presence of base to give compound 6. Deprotection followed by amide formation with glycine 8 provided 9. C—N bond formation between compound 9 and Ar-LG 10 (LG: leaving group such as I, Br or OTf) gave compounds of Formula I. R$^1$ ester in formula I was hydrolyzed to the corresponding carboxylic acid Ia (R$^1$=H).

Alternatively, the compounds of Formula I can be prepared according to Scheme 2 wherein the aromatic group Ar was introduced in the first step. The remaining transformations are similar to those illustrated in Scheme 1.

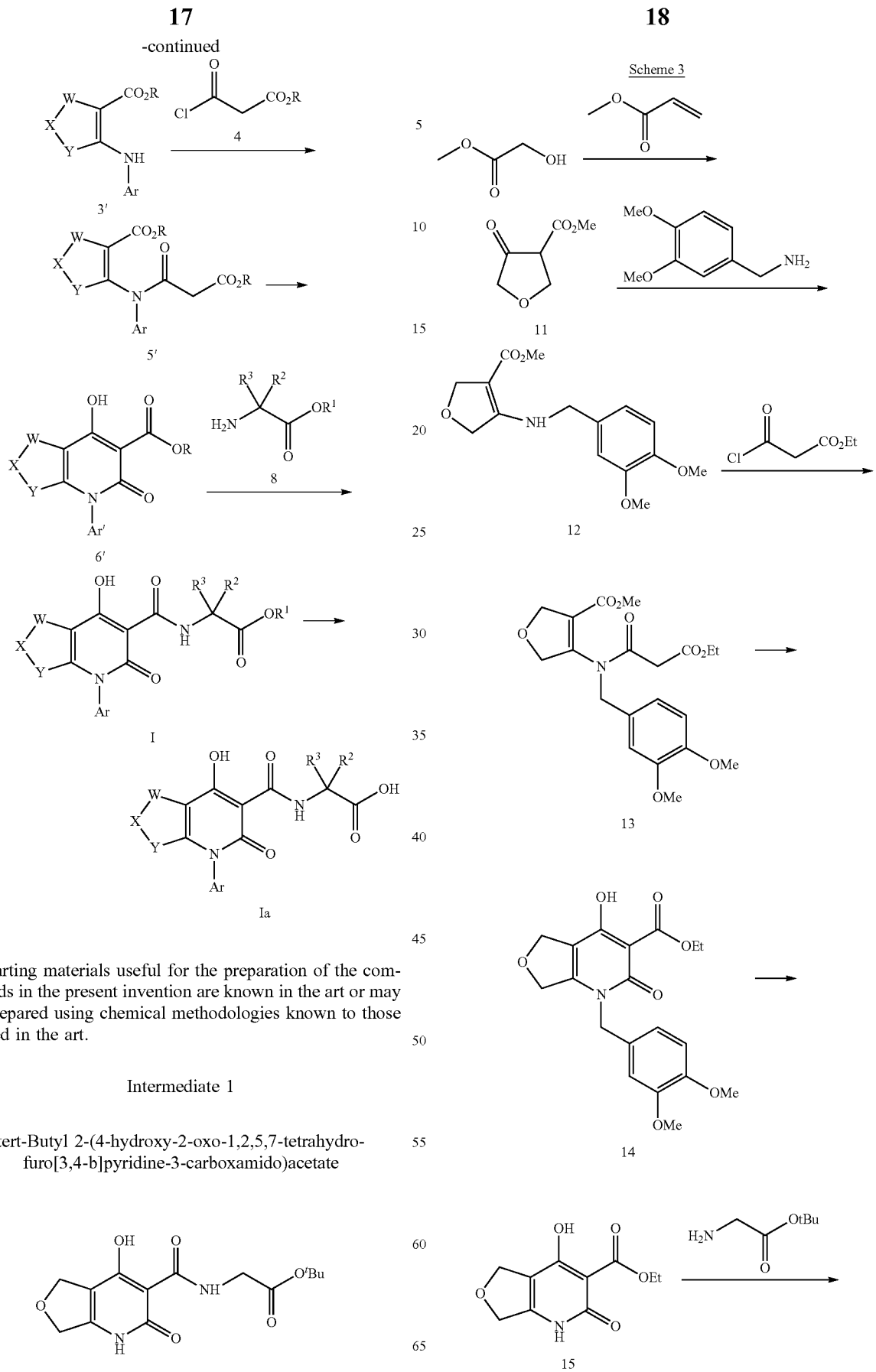
Starting materials useful for the preparation of the compounds in the present invention are known in the art or may be prepared using chemical methodologies known to those skilled in the art.
Intermediate 1
tert-Butyl 2-(4-hydroxy-2-oxo-1,2,5,7-tetrahydro-furo[3,4-b]pyridine-3-carboxamido)acetate

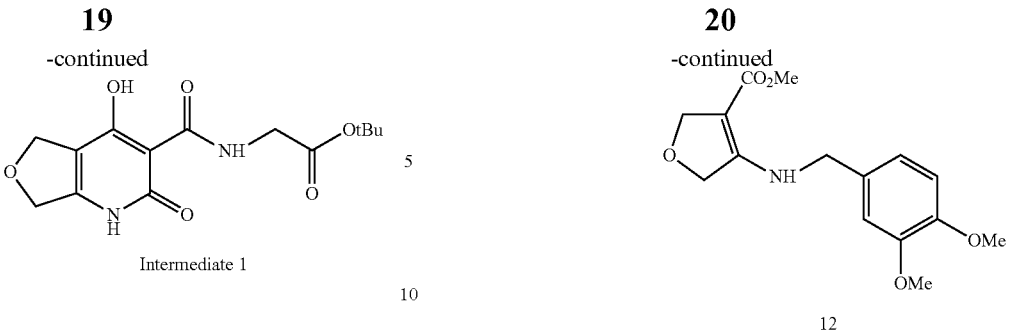

Intermediate 1

Step A. Methyl 4-oxotetrahydrofuran-3-carboxylate (11)

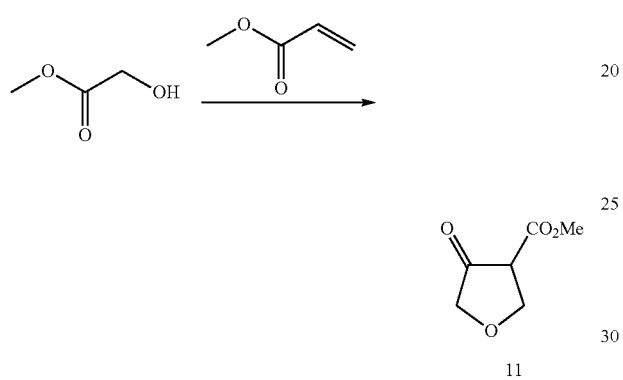

To a suspension of NaH (185 g, 4.6 mol, 60% weight) in THF (4 L) was charged methyl 2-hydroxyacetate (380 g, 4.2 mol) dropwise at 0° C. After the addition, the reaction mixture was stirred for 30 min at ambient temperature and then re-cooled to 0° C. A solution of methyl acrylate (400 g, 4.64 mol) in DMSO (2 L) was added dropwise over 2 hours at 0° C. The resulting reaction mixture was stirred for 30 min at 0° C. and for 2 h at 20° C. After TLC showed that the start material was consumed completely, the mixture was quenched with 1.5 L of 5% $H_2SO_4$ (slowly) and extracted with EtOAc (3 L). The combined organic layers were washed with brine (1 L), dried over $Na_2SO_4$, filtered and concentrated to afford Methyl 4-oxotetrahydrofuran-3-carboxylate (11) as a liquid. The crude oil was used in the next step without further purification. $^1$H NMR (CDCl$_3$, 400 MHz) δ: 4.35-4.45 (m, 2H), 3.86-3.97 (m, 2H), 3.72 (s, 3H), 3.47 (t, 1H).

Step B. Methyl 4-((3,4-dimethoxybenzyl)amino)-2,5-dihydrofuran-3-carboxylate (12)

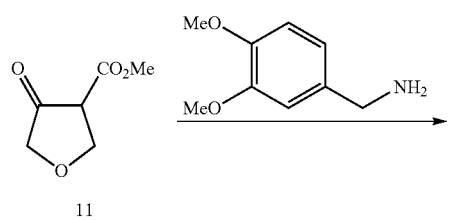

To a solution of (3,4-dimethoxyphenyl)methanamine (212 g, 1.27 mol) in anhydrous ethanol (1.1 L) was added dropwise the solution of crude 11 (300 g, assay 55% 1.15 mol) in anhydrous ethanol (1.1 L) over 30 min using an addition funnel at 90° C. (note: slow addition is crucial to good yield). The reaction was subsequently aged at 90° C. for 1 h. After the reaction was complete shown by LCMS, the reaction was cooled to ambient temperature and concentrated. The crude residual was purified by trituration with methanol (5 V) to give methyl 4-((3,4-dimethoxybenzyl)amino)-2,5-dihydrofuran-3-carboxylate (12) as a solid. $^1$H NMR (CDCl$_3$, 400 MHz) δ: 7.08 (m, 1H), 6.46 (m, 2H), 4.76 (m, 4H), 4.19 (m, 2H), 3.81 (s, 3H), 3.81 (s, 3H), 3.69 (s, 3H), 2.69 (t, 1H). LC/MS (m/z): 294 (M+H)$^+$.

Step C. Methyl 4-(N-(3,4-dimethoxybenzyl)-3-ethoxy-3-oxopropanamido)-2,5-dihydrofuran-3-carboxylate (13)

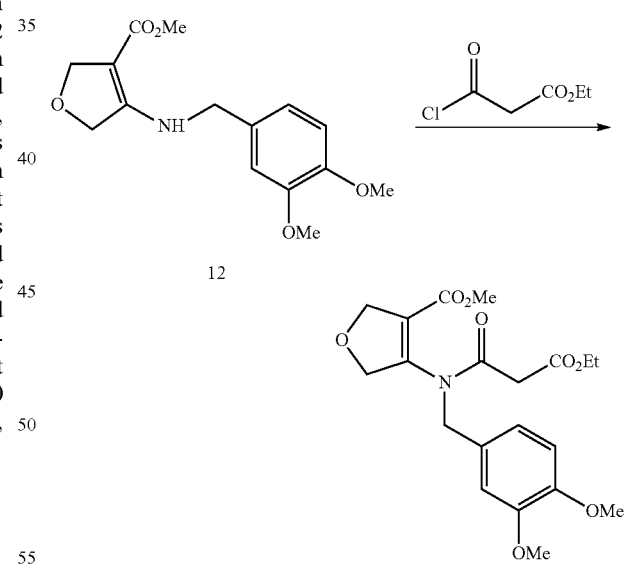

To a solution of 12 (275 g, 0.94 mol) and pyridine (225 g, 2.82 mol) in anhydrous DCM (2.5 L) was charged slowly ethyl 3-chloro-3-oxopropanoate (254 g, 1.69 mol) under nitrogen atmosphere at 0° C. The mixture was warmed to 25° C. and aged for 12 h. After the reaction was complete as shown by LCMS, the reaction was diluted with water and extracted with EtOAc (4 L). The combined organic phases were further washed with sat. NaHCO$_3$, followed by brine. The organic layer was dried over Na$_2$SO$_4$, filtered, and concentrated. The crude residue was purified by flash chromatography on silica gel (EtOAc/PE=1/10) to give methyl 4-(N-(3,4-dimethoxybenzyl)-3-ethoxy-3-oxopropanamido)-2,5-dihydrofuran-3-carboxylate (13) as a solid. $^1$H NMR (CDCl$_3$, 400 MHz) δ: 6.78 (m, 1H), 6.70 (m, 2H), 4.75 (m, 2H), 4.66 (s, 2H), 4.47 (m, 2H), 4.14 (m, 2H), 3.80 (d, 6H), 3.59 (s, 3H), 3.46 (s, 2H), 1.20 (t, 6H). LC/MS (m/z): 408 (M+H)$^+$.

Step D. Ethyl 1-(3,4-dimethoxybenzyl)-4-hydroxy-2-oxo-1,2,5,7-tetrahydrofuro[3,4-b]pyridine-3-carboxylate (14)

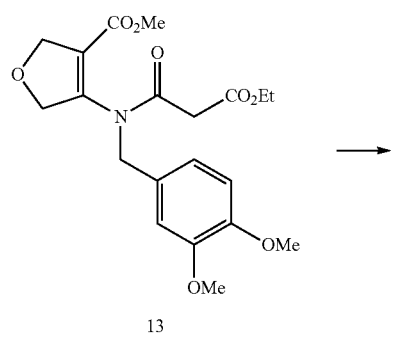

13

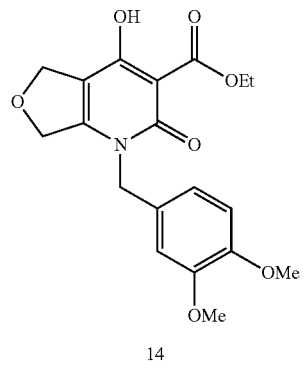

14

To a solution of 13 (190 g, 0.47 mol) in anhydrous ethanol (2 L) was charged NaH (24.7 g, 0.61 mol, 60% weight) in portions at ambient temperature. The mixture was aged at 25° C. for 1 h. After the reaction was complete shown by LCMS, the reaction was quenched with sat. NH$_4$Cl, and extracted with EtOAc (4 L). The combined organic solution was dried over Na$_2$SO$_4$, filtered, and concentrated. The crude residue was further purified by trituration with methanol (4 V) to give Ethyl 1-(3,4-dimethoxybenzyl)-4-hydroxy-2-oxo-1,2,5,7-tetrahydrofuro[3,4-b]pyridine-3-carboxylate (14) as a solid. $^1$H NMR (CDCl$_3$, 400 MHz) δ: 6.73 (m, 1H), 6.65 (m, 2H), 4.95 (m, 4H), 4.83 (s, 2H), 4.41 (q, 2H), 3.78 (d, 6H), 1.36 (t, 3H). LC/MS (m/z): 376 (M+H)$^+$.

Step E. Ethyl 4-hydroxy-2-oxo-1,2,5,7-tetrahydrofuro[3,4-b]pyridine-3-carboxylate (15)

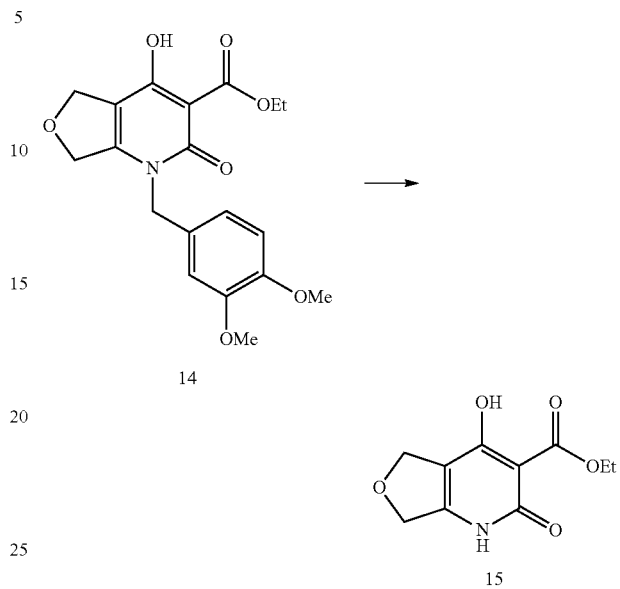

A solution of 14 (150 g, 0.4 mol) in TFA (1200 g, 12 mol) was heated at 70° C. for 24 h under nitrogen. After the reaction was complete shown by LCMS, the reaction was cooled to room temperature and azeotroped off TFA with ACN to afford a black crude material. The residue was further purified by flash chromatography on silica gel (EtOAc/PE=1/3) to give ethyl 4-hydroxy-2-oxo-1,2,5,7-tetrahydrofuro[3,4-b]pyridine-3-carboxylate (15) as a solid. $^1$H NMR (CDCl$_3$, 400 MHz) δ: 4.95 (d, 2H), 4.92 (d, 2H), 4.36 (q, 2H), 1.38 (t, 3H). LC/MS (m/z): 226 (M+H)$^+$.

Step F. tert-Butyl 2-(4-hydroxy-2-oxo-1,2,5,7-tetrahydrofuro[3,4-b]pyridine-3-carboxamido)acetate (Intermediate 1)

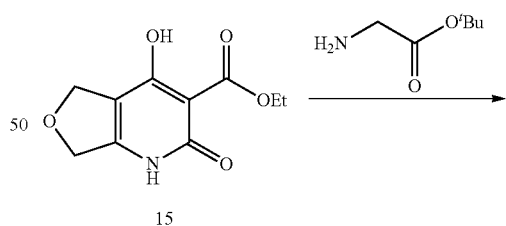

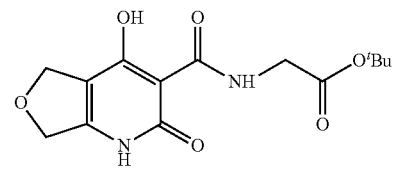 [SMILES: CC(C)(C)OC(=O)CNC(=O)c1c(O)c2c([nH]c1=O)COC2]

Intermediate 1

A solution of 15 (35 g, 0.15 mol) and tert-butyl 2-aminoacetate (30 g, 0.23 mol) in IPA (500 mL) was heated at 100° C. for 16 h. After the reaction was complete shown by LCMS, the reaction was cooled to rt, diluted with water and extracted with EtOAc (1 L). The combined organic phases were dried over Na₂SO₄, filtered, and concentrated. The crude residue was further purified by trituration with methanol (5 V) to give tert-Butyl 2-(4-hydroxy-2-oxo-1,2,5,7-tetrahydrofuro[3,4-b]pyridine-3-carboxamido)acetate (Intermediate 1) as a solid. ¹H NMR (CDCl₃, 400 MHz) δ: 10.1 (s, 1H), 4.84 (d, 4H), 4.05 (s, 2H), 1.37 (s, 9H). LC/MS (m/z): 311 (M+H)⁺.

Intermediate 2 tert-Butyl 2-(1-(4-bromophenyl)-4-hydroxy-2-oxo-1,2,5,7-tetrahydrofuro[3,4-b]pyridine-3-carboxamido)acetate

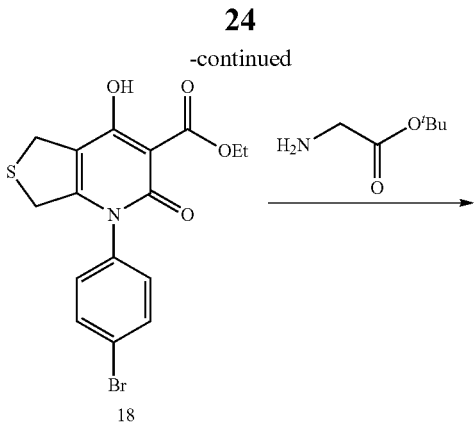

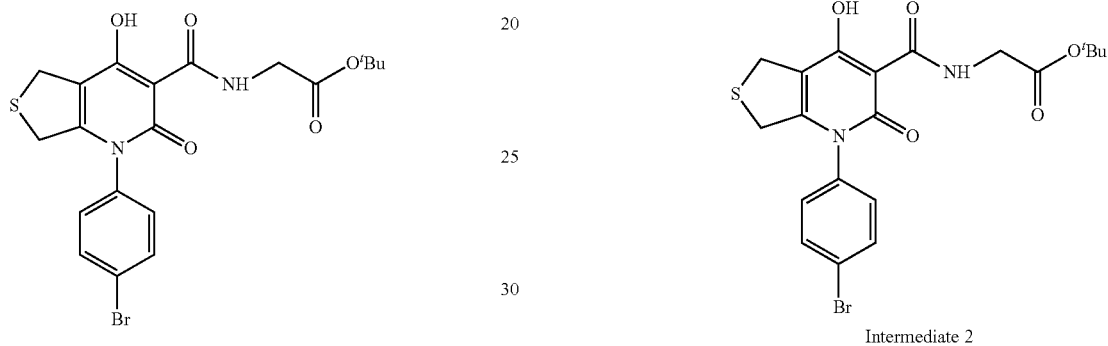

Intermediate 2

Step A. Methyl 4-((4-bromophenyl)amino)-2,5-dihydrofuran-3-carboxylate (16)

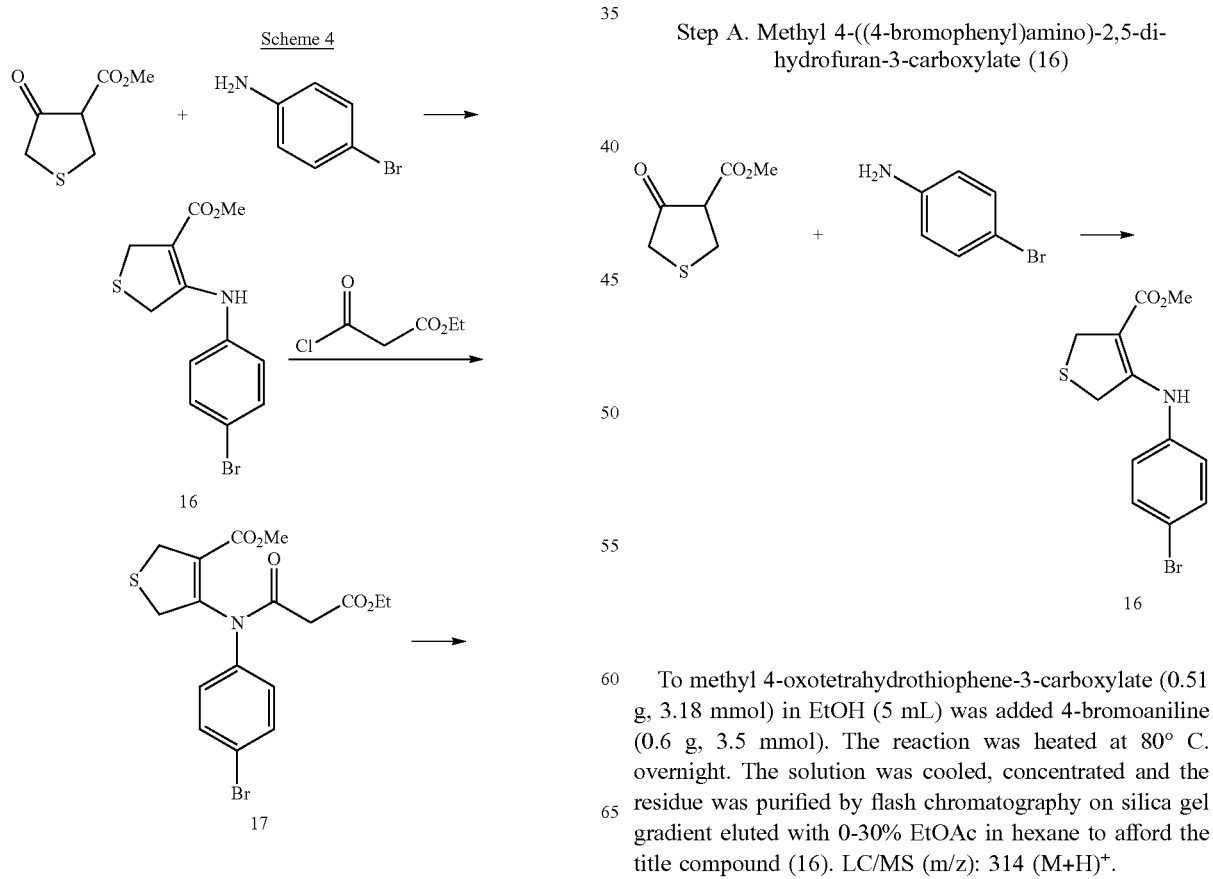

To methyl 4-oxotetrahydrothiophene-3-carboxylate (0.51 g, 3.18 mmol) in EtOH (5 mL) was added 4-bromoaniline (0.6 g, 3.5 mmol). The reaction was heated at 80° C. overnight. The solution was cooled, concentrated and the residue was purified by flash chromatography on silica gel gradient eluted with 0-30% EtOAc in hexane to afford the title compound (16). LC/MS (m/z): 314 (M+H)⁺.

Step B. Methyl 4-(N-(4-bromophenyl)-3-ethoxy-3-oxopropanamido)-2,5-dihydrofuran-3-carboxylate (17)

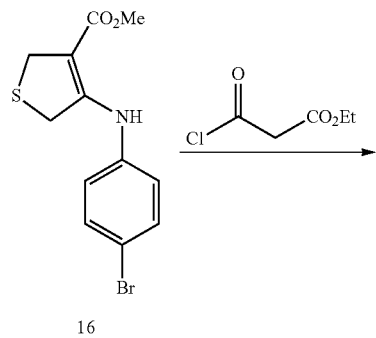

To the product of A (0.510 g, 1.62 mmol) in MeCN (10 mL) was added methyl 3-chloro-3-oxopropanoate (0.435 mL, 4.06 mmol). The mixture was stirred 5 hr at 50° C. and was allowed to come to ambient temperature overnight. The reaction was concentrated and then diluted with EtOAc, washed with saturated aq NaHCO₃, brine, dried (Na₂SO₄), filtered and concentrated. The residue (crude 17) was used directly in next step.

Step C. Ethyl 1-(4-bromophenyl)-4-hydroxy-2-oxo-1,2,5,7-tetrahydrofuro[3,4-b]pyridine-3-carboxylate (18)

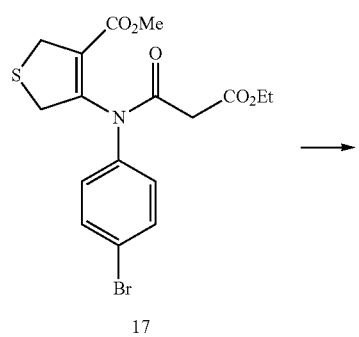

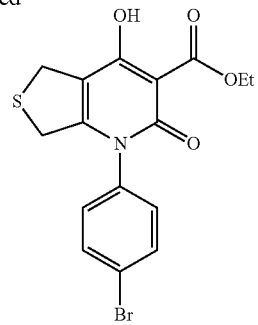

To the crude product of Step B (0.740 g, 1.78 mol) in MeOH (5 mL) was added sodium methoxide (0.817 mL, 3.57 mmol, 25 wt %) at rt. After 15 min acetic acid (0.205 mL, 3.57 mmol) was added. The reaction was concentrated and diluted with EtOAc and washed with aq HCl (2M) and then water. The organic layer was dried (Na₂SO₄), filtered and concentrated. The residue was purified by flash chromatography on silica gel gradient eluted with 0-30% EtOAc in hexane to afford the title compound impure. Residue was dissolved in EA (20 mL) and heated at 40° C. for 10 mins. The solution was allowed to come to ambient temperature and hexanes were added. Solids were isolated to afford title compound (18). LC/MS (m/z): 382 (M+H)⁺.

Step D. tert-butyl 2-(1-(4-bromophenyl)-4-hydroxy-2-oxo-1,2,5,7-tetrahydrofuro[3,4-b]pyridine-3-carboxamido)acetate (Intermediate 2)

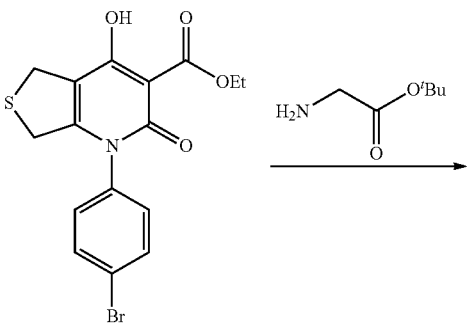

To the product of Step C (0.170 g, 0.445 mmol) in 1-propanol (5 mL) was added tert-butyl glycinate (0.122 mL, 0.890 mmol). The reaction was stirred at 105° C. for 2 hours and was allowed to come to ambient temperature overnight to crystallize. The mixture was concentrated and the product was suspended in i-PrOH and isolated by filtration to afford the title compound (Intermediate 2). Parent mass was not observed by HPLC/MS.

Example 1

2-(4-Hydroxy-2-oxo-1-(4-(trifluoromethyl)phenyl)-1,2,5,7-tetrahydrofuro[3,4-b]pyridine-3-carboxamido)acetic acid

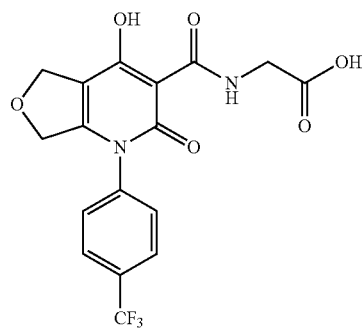 [SMILES: O=C(O)CNC(=O)c1c(O)c2c(n(-c3ccc(C(F)(F)F)cc3)c1=O)COC2]

Step A: Tert-butyl 2-(4-hydroxy-2-oxo-1-(4-(trifluoromethyl)phenyl)-1,2,5,7-tetrahydrofuro[3,4-b]pyridine-3-carboxamido)acetate To a mixture of tert-butyl 2-(4-hydroxy-2-oxo-1,2,5,7-tetrahydrofuro[3,4-b]pyridine-3-carboxamido)acetate (Intermediate 1, 50 mg, 0.161 mmol), 1-iodo-4-(trifluoromethyl)benzene (43.8 mg, 0.161 mmol), copper (I) iodide (6.14 mg, 0.032 mmol), tetrabutylammonium iodide (11.90 mg, 0.032 mmol), and 2-acetylcyclohexanone (11.29 mg, 0.081 mmol) in N,N-dimethylacetamide (1.5 ml), $Cs_2CO_3$ (158 mg, 0.483 mmol) was added. The reaction mixture was stirred at 100° C. overnight. EtOAc (20 mL) was added to the reaction and after the organic layer was washed with water (15 mL) and brine (15 mL), it was dried with $MgSO_4$, filtered and concentrated in vacuo. The residue was purified by prep TLC eluting with 5% MeOH in DCM to afford the desired product (Rf=0.25 at 5% MeOH in DCM). $^1$H NMR (CDCl$_3$, 500 MHz) δ: 10.24 (broad t, 1H), 7.84 (d, 2H), 7.43 (d, 2H), 5.18 (app t, 2H), 4.64 (app t, 2H), 4.08 (app d, 2H), 1.50 (s, 9H). LC/MS (m/z): 455 (M+H)$^+$.

Step B: 2-(4-Hydroxy-2-oxo-1-(4-(trifluoromethyl)phenyl)-1,2,5,7-tetrahydrofuro[3,4-b]pyridine-3-carboxamido)acetic acid To a solution of tert-butyl 2-(4-hydroxy-2-oxo-1-(4-(trifluoromethyl)phenyl)-1,2,5,7-tetrahydrofuro[3,4-b]pyridine-3-carboxamido)acetate (product of Step A, 17 mg, 0.037 mmol) in DCM (1 ml) was added TFA (0.029 ml, 0.374 mmol). The mixture was stirred at rt for 3 h and the TLC suggested the reaction was complete. The reaction mixture was concentrated to dryness and residual TFA was removed by azitropically evaporating with ACN (2 mL×3). The solid was triturated with cold diethyl ether (cooled by icy-water), filtered through a funnel and air dried to afford the title compound. $^1$H NMR (DMSO-d$_6$, 500 MHz) δ: 10.04 (broad s, 1H), 7.93 (d, 2H), 7.71 (d, 2H), 4.98 (broad s, 2H), 4.63 (broad d, 2H), 3.98 (broad s, 2H). LC/MS (m/z): 399 (M+H)$^+$. Human HIF-PHD2 IC$_{50}$: 5.8 nM.

Examples 2-10 in Table 1 were prepared following the similar procedures described in Example 1 and using Intermediate 1 and appropriate starting materials.

TABLE 1

| Examples | Name | Structure | MS m/z (M + 1)$^+$ and human HIF-PHD2 IC$_{50}$ |
|---|---|---|---|
| Example 2 | 2-(1-(4-chlorophenyl)-4-hydroxy-2-oxo-1,2,5,7-tetrahydrofuro[3,4-b]pyridine-3-carboxamido)acetic acid | 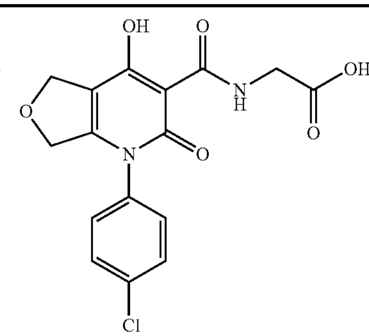 | (M + 1)$^+$ 365 IC$_{50}$ 7.8 nM |
| Example 3 | 2-(1-(4-fluorophenyl)-4-hydroxy-2-oxo-1,2,5,7-tetrahydrofuro[3,4-b]pyridine-3-carboxamido)acetic acid | 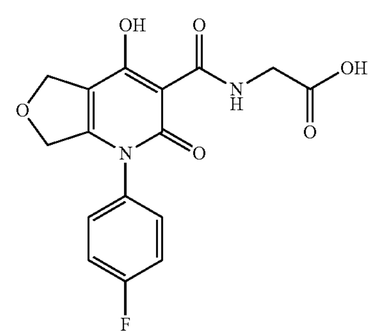 [SMILES: O=C(O)CNC(=O)c1c(O)c2c(n(-c3ccc(F)cc3)c1=O)COC2] | (M + 1)$^+$ 349 IC$_{50}$ 14.1 nM |

TABLE 1-continued

| Examples | Name | Structure | MS m/z (M + 1)+ and human HIF-PHD2 IC$_{50}$ |
|---|---|---|---|
| Example 4 | 2-(4-hydroxy-2-oxo-1-phenyl-1,2,5,7-tetrahydrofuro[3,4-b]pyridine-3-carboxamido)acetic acid | 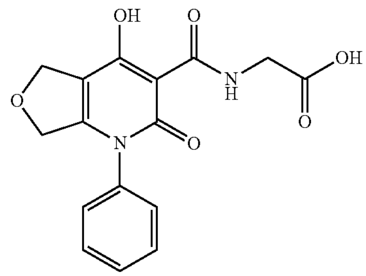 [SMILES: O=C(O)CNC(=O)c1c(O)c2c(n(-c3ccccc3)c1=O)COC2] | (M + 1)+ 331<br>IC$_{50}$ 8.5 nM |
| Example 5 | 2-(4-hydroxy-1-(4-methoxyphenyl)-2-oxo-1,2,5,7-tetrahydrofuro[3,4-b]pyridine-3-carboxamido)acetic acid | 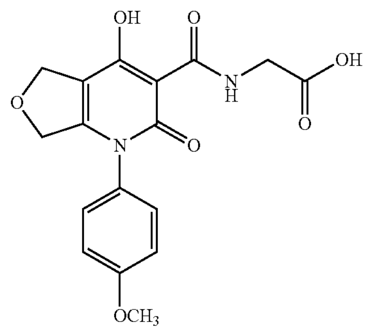 [SMILES: COc1ccc(-n2c3c(c(O)c(C(=O)NCC(=O)O)c2=O)COC3)cc1] | (M + 1)+ 361<br>IC$_{50}$ 11.4 nM |
| Example 6 | 2-(4-hydroxy-2-oxo-1-(4-(trifluoromethoxy)phenyl)-1,2,5,7-tetrahydrofuro[3,4-b]pyridine-3-carboxamido)acetic acid | 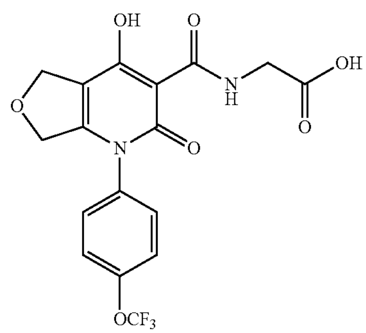 [SMILES: O=C(O)CNC(=O)c1c(O)c2c(n(-c3ccc(OC(F)(F)F)cc3)c1=O)COC2] | (M + 1)+ 415<br>IC$_{50}$ 13.4 nM |
| Example 7 | 2-(4-hydroxy-2-oxo-1-(m-tolyl)-1,2,5,7-tetrahydrofuro[3,4-b]pyridine-3-carboxamido)acetic acid | 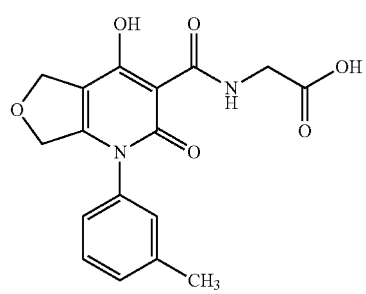 [SMILES: Cc1cccc(-n2c3c(c(O)c(C(=O)NCC(=O)O)c2=O)COC3)c1] | (M + 1)+ 345<br>IC$_{50}$ 8.6 nM |
| Example 8 | 2-(4-hydroxy-2-oxo-1-(p-tolyl)-1,2,5,7-tetrahydrofuro[3,4-b]pyridine-3-carboxamido)acetic acid | 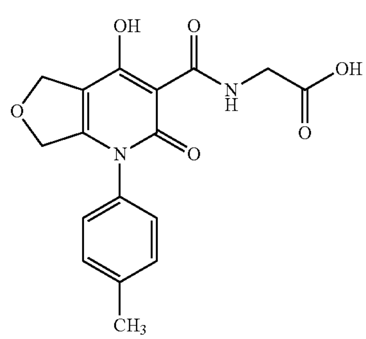 [SMILES: Cc1ccc(-n2c3c(c(O)c(C(=O)NCC(=O)O)c2=O)COC3)cc1] | (M + 1)+ 345<br>IC$_{50}$ 10.0 nM |

TABLE 1-continued

| Examples | Name | Structure | MS m/z (M + 1)+ and human HIF-PHD2 IC$_{50}$ |
|---|---|---|---|
| Example 9 | 2-(1-(4-cyanophenyl)-4-hydroxy-2-oxo-1,2,5,7-tetrahydrofuro[3,4-b]pyridine-3-carboxamido)acetic acid | 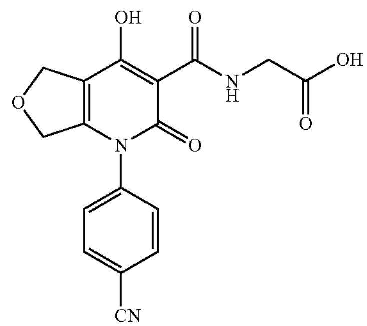 [SMILES: N#Cc1ccc(-n2c3c(c(O)c(C(=O)NCC(=O)O)c2=O)COC3)cc1] | (M + 1)+ 356 IC$_{50}$ 9.5 nM |
| Example 10 | 2-(4-hydroxy-1-(5-methoxypyridin-2-yl)-2-oxo-1,2,5,7-tetrahydrofuro[3,4-b]pyridine-3-carboxamido)acetic acid | 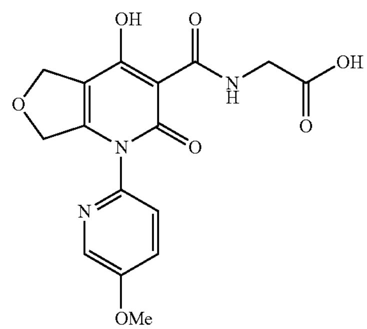 [SMILES: COc1ccc(-n2c3c(c(O)c(C(=O)NCC(=O)O)c2=O)COC3)nc1] | (M + 1)+ 362 IC$_{50}$ 14.2 nM |

Example 11

2-(1-(4-Bromophenyl)-4-hydroxy-2-oxo-1,2,5,7-tetrahydrothieno[3,4-b]pyridine-3-carboxamido)acetic acid

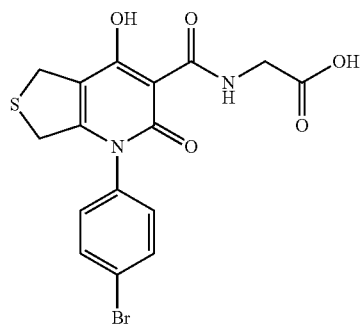 [SMILES: O=C(O)CNC(=O)c1c(O)c2c(n(-c3ccc(Br)cc3)c1=O)CSC2]

To Intermediate 2 (0.060 g, 0.125 mmol) was added CH$_2$Cl$_2$ (1 mL) and TFA (0.5 mL) at rt. After 2 hr the reaction was diluted with MeOH (5 mL) to crystallize the product. The mixture was concentrated and then diluted with MeOH. The crystals were isolated by filtration and washed twice with MeOH and once with hexane to afford the title compound. LC/MS (m/z): 425 (M+H)+. Human HIF-PHD2 IC$_{50}$: 8.8 nM.

Example 12

2-(4-Hydroxy-2-oxo-1-((4'-(trifluoromethoxy)-[1,1'-biphenyl]-4-yl)methyl)-1,2,5,7-tetrahydrothieno[3,4-b]pyridine-3-carboxamido)acetic acid

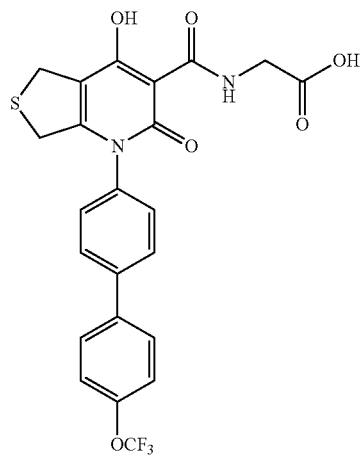 [SMILES: O=C(O)CNC(=O)c1c(O)c2c(n(-c3ccc(-c4ccc(OC(F)(F)F)cc4)cc3)c1=O)CSC2]

Step A: Tert-butyl 2-(4-hydroxy-2-oxo-1-((4'-(trifluoromethoxy)-[1,1'-biphenyl]-4-yl)methyl)-1,2,5,7-tetrahydrothieno[3,4-b]pyridine-3-carboxamido)acetate Intermediate 2 (0.05 g, 0.104 mmol) was dissolved in DMA (0.8 mL) in a 10 mL reaction tube of a CEM Corporation Discover 300 Watt microwave reactor. An aq solution of $Na_2CO_3$ (2 M, 0.104 mL, 0.208 mmol), (4-(trifluoromethoxy)phenyl)boronic acid (38.5 mg, 0.187 mmol) and bis(triphenylphosphine)palladium(II) chloride (7.3 mg, 0.010 mmol) were added and the tube was purged with nitrogen, capped and inserted into the microwave reactor. It was heated at 110° C., 50 watts maximum power, for 12 min. The reaction was diluted with EtOAc, washed with 2 M HCl, dried ($Na_2SO_4$), filtered and concentrated. The residue was purified by semi-preparative reverse phase HPLC on a C18 column eluted with 0-100% MeCN in water. The desired fractions were concentrated, dissolved in EtOAc and washed with water. The organic layer was dried ($Na_2SO_4$), filtered and concentrated affording the title compound. Parent mass was not observed by LC/MS.

Step B: 2-(4-Hydroxy-2-oxo-1-((4'-(trifluoromethoxy)-[1,1'-biphenyl]-4-yl)methyl)-1,2,5,7-tetrahydrothieno[3,4-b]pyridine-3-carboxamido) acetic acid Product of Step A (12 mg, 0.021 mmol) was dissolved in DCM (1 mL) and TFA (0.5 mL) was added. The reaction was stirred at ambient temperature for 1 h. The reaction was concentrated and washed with hexanes affording the title compound. LC/MS (m/z): 507 (M+H)$^+$. Human HIF-PHD2 $IC_{50}$: 10 nM.

Using the general Suzuki coupling procedures described in Example 12 and the appropriate starting materials the title compound of Example 13 was obtained as shown in Table 2.

330:74-80 (2004); Hirsili, M, et al., *J. Bio. Chem.* 278 (33): 30772-30780 (2005); Hyunju, C., et al., *Biochem. Biophys. Res. Comm.* 330 275-280 (2005); and Hewitson, K. S., et al., *Methods in Enzymology*, (Oxygen Biology and Hypoxia); Elsevier Publisher (2007), pg. 25-42 (ISSN: 0076-6879).

The biological activity of the present compounds may be evaluated using assays described herein below:

To each well of a 384-well plate, 1 μL of test compounds in DMSO (final concentration ranging from 0.3 nM to 10 uM) were added into 20 μl of assay buffer (50 mM Tris pH 7.4/0.01% Tween-20/0.1 mg/ml bovine serum albumin/10 μM ferrous sulfate/1 mM sodium ascorbate/20 μg/ml catalase) containing 0.15 μg/ml FLAG-tagged full length PHD2 expressed in and purified from baculovirus-infected Sf9 cells. After a 5 min preincubation at room temperature, the enzymatic reactions were initiated by the addition of 4 μL of substrates {final concentrations of 0.2 μM 2-oxoglutarate and 0.5 μM HIF-1α peptide biotinyl-DLDLEMLAPYIP-MDDDFQL (SEQ ID NO:1)}. After incubation for 45 minutes at room temperature, the reactions were terminated by the addition of a 25 μL quench/detection mix to a final concentration of 1 mM ortho-phenanthroline, 0.1 mM EDTA, 0.5 nM anti-(His)6 LANCE reagent (Perkin-Elmer Life Sciences), 100 nM AF647-labeled streptavidin (Invitrogen), and 2 μg/ml (His)6-VHL complex {S. Tan Protein Expr. Purif. 21, 224-234 (2001)} and the signals were developed for 30 minutes at room temperature. The ratio of time resolved fluorescence signals at 665 and 620 nm was

TABLE 2

| Example | Name | Structure | MS m/z (M + 1)$^+$ and human HIF-PHD2 $IC_{50}$ |
|---|---|---|---|
| Example 13 | 2-(4-Hydroxy-2-oxo-1-(3'-(trifluoromethoxy)-[1,1'-biphenyl]-4-yl)-1,2,5,7-tetrahydrothieno[3,4-b]pyridine-3-arboxamido) acetic acid | 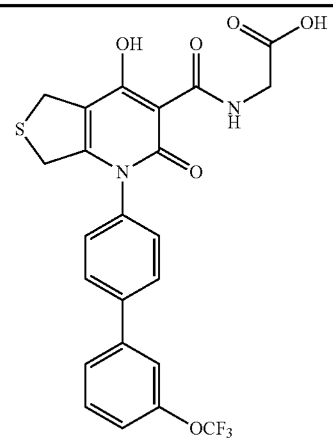 | (M + 1)$^+$ 507 $IC_{50}$: 4.1 nM |

Biological Assays

The exemplified compounds of the present invention have been found to inhibit the hydroxylation of a HIF peptide by PHD2 and exhibit $IC_{50}$ values ranging between 0.1 nanomolar to 10 micromolar. Select examples of assays that may be used to detect favorable activity are disclosed in the following publications: Oehme, F., et al., *Anal. Biochem.* determined, and percent inhibition was calculated relative to the high control samples (DMSO treated) run in parallel, after background subtraction.

Inhibition of the catalytic activity of HIF-PHD1 and HIF-PHD3 can be determined similarly, except for HIF-PHD3, final concentrations of 4 μM 2-oxoglutarate is used during the reaction.

What is claimed is:

1. A compound which is:

2-(4-Hydroxy-2-oxo-1-(4-(trifluoromethyl)phenyl)-1,2,5,7-tetrahydrofuro[3,4-b]pyridine-3-carboxamido)acetic acid;

2-(1-(4-chlorophenyl)-4-hydroxy-2-oxo-1,2,5,7-tetrahydrofuro[3,4-b]pyridine-3-carboxamido)acetic acid;

2-(1-(4-fluorophenyl)-4-hydroxy-2-oxo-1,2,5,7-tetrahydrofuro[3,4-b]pyridine-3-carboxamido)acetic acid;

2-(4-hydroxy-2-oxo-1-phenyl-1,2,5,7-tetrahydrofuro[3,4-b]pyridine-3-carboxamido)acetic acid;

2-(4-hydroxy-1-(4-methoxyphenyl)-2-oxo-1,2,5,7-tetrahydrofuro[3,4-b]pyridine-3-carboxamido)acetic acid;

2-(4-hydroxy-2-oxo-1-(4-(trifluoromethoxy)phenyl)-1,2,5,7-tetrahydrofuro[3,4-b]pyridine-3-carboxamido)acetic acid;

2-(4-hydroxy-2-oxo-1-(m-tolyl)-1,2,5,7-tetrahydrofuro[3,4-b]pyridine-3-carboxamido)acetic acid;

2-(4-hydroxy-2-oxo-1-(p-tolyl)-1,2,5,7-tetrahydrofuro[3,4-b]pyridine-3-carboxamido)acetic acid;

2-(1-(4-cyanophenyl)-4-hydroxy-2-oxo-1,2,5,7-tetrahydrofuro[3,4-b]pyridine-3-carboxamido)acetic acid; and 2-(4-hydroxy-1-(5-methoxypyridin-2-yl)-2-oxo-1,2,5,7-tetrahydrofuro[3,4-b]pyridine-3-carboxamido)acetic acid;

or a pharmaceutically acceptable salt thereof.

2. A pharmaceutical composition comprising a compound of claim 1 and pharmaceutically acceptable carrier.

3. A method for the treatment of anemia in a mammal which comprises administering to the mammal an effective amount of a compound of claim 1, or a pharmaceutically acceptable salt thereof.

* * * * *

SEQUENCE LISTING

<160> NUMBER OF SEQ ID NOS: 1

<210> SEQ ID NO 1
<211> LENGTH: 19
<212> TYPE: PRT
<213> ORGANISM: Artificial Sequence
<220> FEATURE:
<223> OTHER INFORMATION: Completely Synthetic Amino Acid Sequence

<400> SEQUENCE: 1

```
Asp Leu Asp Leu Glu Met Leu Ala Pro Tyr Ile Pro Met Asp Asp
1               5                   10                  15

Phe Gln Leu
```